United States Patent [19]

Sánchez Cordero

[11] 4,428,389
[45] Jan. 31, 1984

[54] DENTAL FLOSS DISPENSER ADAPTED TO THE CAP OF THE COMMON TOOTHPASTE

[76] Inventor: Sergio Sánchez Cordero, Amores #28-PB Col. del Valle, Mexico 12 D.F. Mexico City, Mexico

[21] Appl. No.: 198,123

[22] Filed: Oct. 17, 1980

[51] Int. Cl.³ .......................................... A61C 15/00
[52] U.S. Cl. ............................ 132/92 A; 132/79 E; 222/93
[58] Field of Search .............. 132/90, 91, 92 R, 92 A, 132/79 E; 222/93

[56] References Cited

U.S. PATENT DOCUMENTS

| 301,055 | 6/1884 | Greene | 132/92 A |
|---|---|---|---|
| 1,279,507 | 9/1918 | Briggs | 132/92 A |
| 1,466,982 | 9/1923 | Bailey | 132/79 E |
| 1,488,810 | 4/1924 | Fraser | 132/79 E |
| 1,492,836 | 5/1924 | Decker | 132/79 E |
| 1,614,260 | 1/1927 | Siewart | 132/92 R |
| 1,733,114 | 10/1929 | Brennan | 132/79 E |
| 1,858,134 | 5/1932 | Booth et al. | 132/79 E |
| 2,233,522 | 3/1941 | Fickle | 132/92 R |
| 3,178,060 | 4/1965 | Bossack | 222/93 |
| 3,718,146 | 2/1973 | Myers | 132/92 R |
| 3,906,963 | 9/1975 | Jenkins et al. | 132/92 A |

Primary Examiner—Paul J. Hirsch

[57] ABSTRACT

This invention relates to a specially designed dental floss dispenser that fits over the closure cap and upper portion of the common toothpaste tube. The purpose of it is to market both products together so that the community already using the toothpaste as a regular method of oral hygiene can benefit from the incorporation of the use of the dental floss. This has been accomplished without having to change anything of the original parts of the toothpaste tube or its closure cap. The dispenser has been provided with an internal socket so dimensioned as to receive almost every closure cap of toothpaste tubes in the market, being of great advantage for both manufacturers and consumers as well. Further, the dispenser can be separated from the closure cap easily, giving the choice to the consumer of using it as an integrated part of the toothpaste tube, carrying it with him through the day without leaving the toothpaste tube capless, or fitting it over the closure cap of a newly bought toothpaste tube which can be of a different brand and size.

1 Claim, 3 Drawing Figures

DENTAL FLOSS DISPENSER ADAPTED TO THE CAP OF THE COMMON TOOTHPASTE

BACKGROUND OF THE INVENTION

It is well known and accepted by the dental community the fact that the dental floss is a useful tool when incorporated in the oral hygiene habits of a population and significantly increases the dental health status of its individuals.

The dental floss contributes to oral hygiene and thus to oral health by removing interdental bacterial plaque from the teeth. The toothbrush can get mechanically to those areas and reach the dental plaque and remove it. Unremoved interdental plaque will cause gingivitis (inflammation of the gums) and after this will progress into periodontal breakdown known as periodontitis (destruction of the alveolar bone and supporting structures of the teeth). The major cause of tooth loss of a population above 30 years of age is undoubtedly periodontitis.

Only a small segment of the population that practices daily oral hygiene with regular toothpaste and toothbrush practices dental flossing. A great percentage of these individuals who have already developed the habit of oral hygiene through their lifetimes and moreover the children who are developing one could be enormously beneficiated by the regular practice of interdental flossing. This existing gap is mainly attributed to the relatively newcomming of the dental floss and to other important factors such as: publicity, marketing, psychological, economical and ergonomical factors among others.

The marketing and publicity of the toothpaste and toothbrush have well established channels. The toothpaste has the highest sales volume due to the fact that it less durable than the toothbrush and must be replaced sooner. The marketing and publicity of the dental floss has been very poor trying to convince people that something else besides toothpaste and toothbrush significantly adds to the health, freshness and cleanliness of their mouths and dentitions.

The marketing of both products together is part of the answer to the problem.

DESCRIPTION OF PRIOR ART

The concept of marketing the toothpaste tube and a dental floss dispenser together is not new. Sample patents teaching dental floss dispensers (hereinafter referred to as the dispensers) in relationship to toothpaste tubes (hereinafter referred to as the tubes) and corresponding closure caps (hereinafter referred to as the caps) are disclosed in the following U.S. patents.: U.S. Pat. No. 1,466,982 issued to T. A. Bailey in 1923, U.S. Pat. No. 1,488,810 issued to J. K. Fraser in 1924, U.S. Pat. No. 1,492,836 issued to C. D. Decker in 1924, U.S. Pat. No. 1,614,260 issued to A. D. Siewert in 1927, U.S. Pat. No. 1,733,114 in 1929 and U.S. Pat. No. 1,858,134 issued to H. N. Booth et al. in 1932.

One major difference of the present disclosure in comparison to the above cited patents is that this dispenser has been structured and dimensioned to fit over different sizes of caps and corresponding tubes due to the fact that it is pressure and not a threading mechanism the one that holds the dispenser in place and therefore it will not depend on the characteristics and diameter of the threaded neck of the tube which vary from brand to brand. This features give the present disclosure an enormous versatility for both, manufacturers and consumers.

SUMMARY OF THE INVENTION

A dental floss dispenser has been designed that fits over the cap and upper portion of the common toothpaste tube. It allows the dental floss and toothpaste to be marketed in the same channel. Nothing has to be structurally changed in the toothpaste tube its closure cap or its package in order to be able to accept this dispenser. The dispenser has an internal socket so dimensioned that it will receive different sizes of closure caps of toothpaste tubes in the market. Every time that the consumer opens or closes the tube he is in physical contact with the dispenser due to the fact that the dispenser and cap form one functional closure unit. With a handsome presentation and a proper backing-up publicity on the benefits of regular dental flossing and having already purchased the floss at a lower comparative price (mass distribution allows to cut down on prices) there is no dobut that the consumer will start practicing flossing. Further, the dispenser can be separated from the closure cap easily, giving the choice to the consumer of using it as an integrated part of the toothpaste tube, carrying it with him through the day without leaving the toothpaste tube capless, or fitting it over the closure cap of a newly bought toothpaste tube which can be of a different brand and size.

For the manufacturer means that if he wants to incorporate the dispenser to his brand of toothpaste tube, he does not have to sustitute the cap, avoiding the modification of the established production and/or supplying scheme of cap manufacturing. It also avoids the interference with routine production-line of toothpaste tubing, one possible additional step being the insertion of the dispenser over the cap prior packaging once the tube is filled with toothpaste and with its closure cap in place.

Therefore, it is an object of this invention to provide a versatile dispenser that has an internal socket so dimensioned as to fit over various sizes of closure and upper portion of toothpaste tube forming one functional structure with the cap in the closure of the tube.

It is a further object of this invention to provide a dispenser that if the consumer decides to carry it separately with him during the day, he might do so without leaving the tube capless.

It is a further object to provide a dispenser that if purchased with the tube and its toothpaste is consumed first he might continue using the dispenser by fitting it over another tube not necessarily of the same brand or size.

A still further object of the invention is to provide a dispenser that will establish better conditions so that the people already consuming toothpastes will benefit acquiring the habit of flossing.

These and other objects of the above invention will be apparent from the following description of the drawings and preferred embodiment of the invention.

BRIEF DESCRIPTION OF THE DRAWINGS

The full nature of the invention will be understood from the accompanying drawings and the following description and claim.

PREFERRED EMBODIMENT OF THE INVENTION

Figures 1, 2, 3:
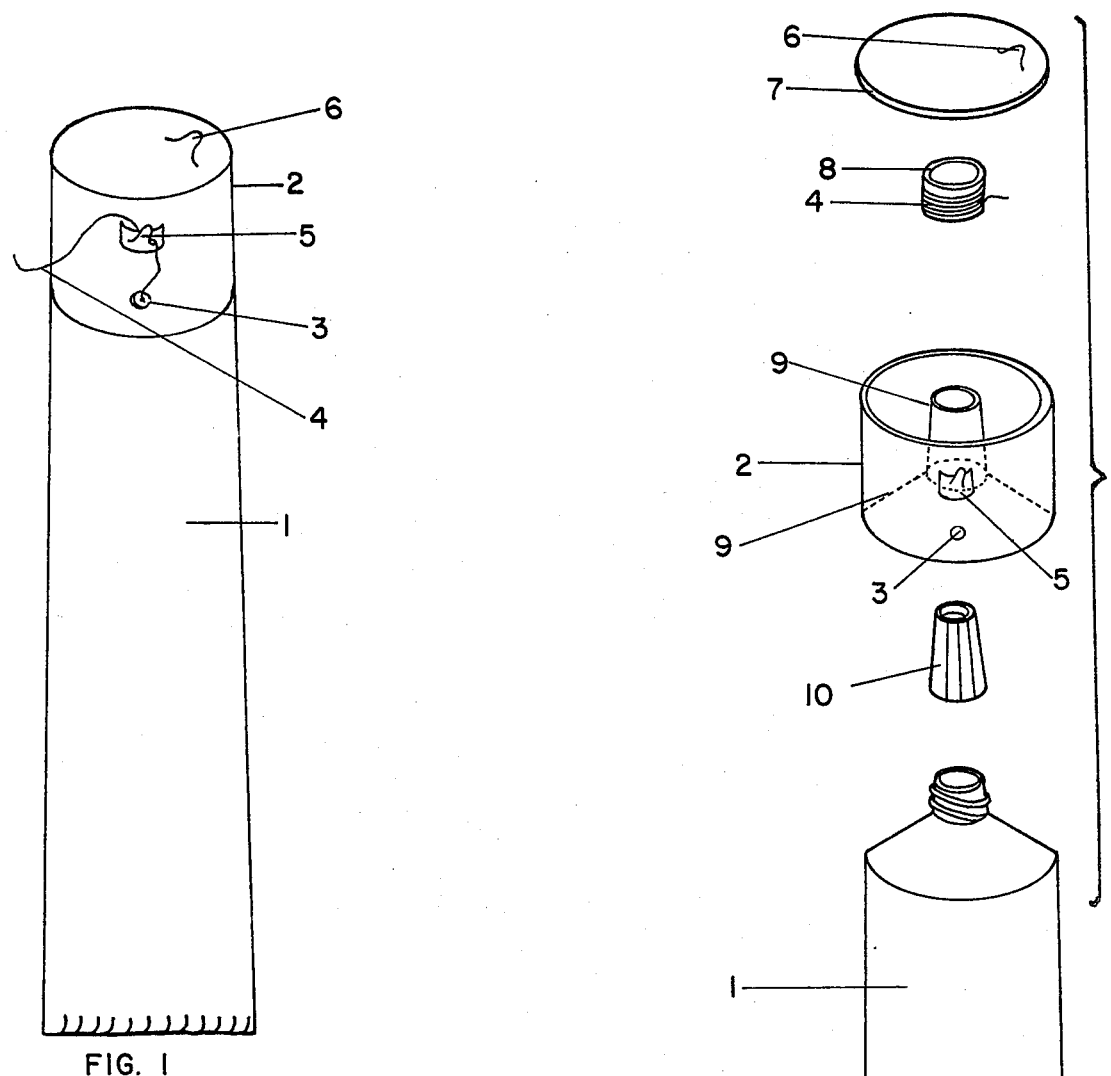
FIG. 1 is a perspective view of the dispenser assembled with the closure cap of the tube sitting on the top of said tube.
FIG. 2 shows the dispenser disassembled to show its constituting parts or elements in an exploded view. The upper part of the tube and corresponding closure cap can be appreciated.
FIG. 3 is a section view to show the details and relationships of its internal structures including the spool containing the dental floss.

For the purposes of promoting an understanding of the principles of the invention, reference will now be made to the embodiment illustrated in the drawing and specific language will be used to describe the same. It will, nevertheless, be understood that no limitation of the scope of the invention is thereby intended, such alterations and further modifications in the illustrated device, and such further applications of the principles of the invention as illustrated therein being contemplated as would occur to one skilled in the art to which the invention relates.

Referring now more particularly to the drawings there is illustrated a dental floss dispenser adapted to the cap 10 and upper portion of the toothpaste tube 1. The dental floss dispenser comprising a main body 2 having a cylindrical outer wall and an opening at the top thereof, a cap 7 for said opening secured to said body 2 by a snap fit, said cap 7 having a protrusion 6 at the top thereof for aiding the removal of said cap 7 from the main body 2, a socket 9 having an outer conical wall extending within said main body 2 and dimensioned to receive the closure cap 10 of the toothpaste tube 1, said socket extending up from a bottom end plane of said main body 2, a spool 8 of dental floss 4 mounted for rotation on the outer wall of said socket 9, an end of the dental floss 4 being threaded thru a small opening 3 in the cylindrical wall of the main body 2 for dispensing of the floss 4, a cutting member 5 mounted on the body 2 for cutting said floss 4 at a desired length.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention and scope of the claim are also desired to be protected.

The invention claimed is:

1. In combination with a toothpaste tube having a closure cap thereon, a dental floss dispenser comprising;
   a main body having a cylindrical outer wall and an opening at the top thereof,
   a cap for said opening secured to said body by a snap fit, said cap having a protrusion at the top thereof for aiding the removal of said cap from the main body,
   a socket having an outer conical wall extending within said main body and dimensioned to receive the closure cap of the toothpaste tube, said socket extending up from a bottom end plane of said main body,
   a spool of dental floss mounted for rotation on the outer wall of said socket, an end of the dental floss being threaded thru a small opening in the cylindrical wall of the main body for dispensing the floss,
   a cutting member mounted on the body for cutting said floss at a desired length.

* * * * *